United States Patent
Hoves et al.

(10) Patent No.: US 10,428,027 B2
(45) Date of Patent: Oct. 1, 2019

(54) SULFINYLPHENYL OR SULFONIMIDOYLPHENYL BENZAZEPINES

(71) Applicant: Hoffmann La-Roche Inc., Little Falls, NJ (US)

(72) Inventors: Sabine Hoves, Habach (DE); Lisha Wang, Basel (CH); Hongying Yun, Shanghai (CN); Weixing Zhang, Shanghai (CN); Wei Zhu, Shanghai (CN)

(73) Assignee: Hoffmann La-Roche Inc., Little Falls, NJ (US)

( * ) Notice: Subject to any disclaimer, the term of this patent is extended or adjusted under 35 U.S.C. 154(b) by 0 days.

(21) Appl. No.: 15/915,563

(22) Filed: Mar. 8, 2018

(65) Prior Publication Data

US 2018/0194735 A1    Jul. 12, 2018

Related U.S. Application Data

(63) Continuation of application No. PCT/EP2016/071613, filed on Sep. 14, 2016.

(30) Foreign Application Priority Data

Sep. 17, 2015    (CN) .................. PCT/CN2015/089868

(51) Int. Cl.
| | |
|---|---|
| *A61K 31/55* | (2006.01) |
| *C07D 223/16* | (2006.01) |
| *C07D 403/04* | (2006.01) |
| *C07D 401/04* | (2006.01) |

(52) U.S. Cl.
CPC ......... *C07D 223/16* (2013.01); *C07D 401/04* (2013.01)

(58) Field of Classification Search
CPC ..... A61K 31/55; C07D 223/16; C07D 403/04
USPC ..................... 514/213.01; 540/593
See application file for complete search history.

(56) References Cited

FOREIGN PATENT DOCUMENTS

| | | |
|---|---|---|
| WO | 2007/024612 A2 | 3/2007 |
| WO | 2011/022508 A2 | 2/2011 |
| WO | 2011/022509 A2 | 2/2011 |
| WO | 2012/097173 A2 | 7/2012 |
| WO | 2016/096778 A1 | 6/2016 |

OTHER PUBLICATIONS

ISR for PCT/EP2016/071613 (dated Oct. 31, 2016).

*Primary Examiner* — Brenda L Coleman
(74) *Attorney, Agent, or Firm* — Brian L. Buckwalter

(57) ABSTRACT

This invention relates to novel sulfinylphenyl or sulfonimidoylphenyl benzazepine compounds of the formula

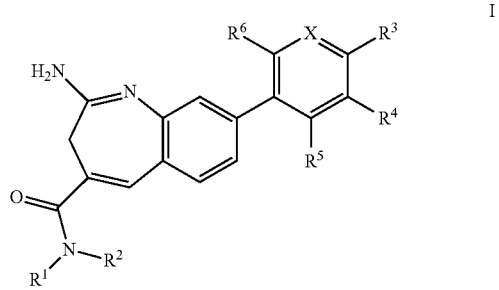

wherein X and $R^1$ to $R^6$ are as defined in the description and in the claims, as well as pharmaceutically acceptable salts thereof. These compounds are TLR agonists and may therefore be useful as medicaments for the treatment of diseases such as cancer, autoimmune diseases, inflammation, sepsis, allergy, asthma, graft rejection, graft-versus-host disease, immunodeficiencies, and infectious diseases.

19 Claims, No Drawings

SULFINYLPHENYL OR SULFONIMIDOYLPHENYL BENZAZEPINES

CROSS REFERENCE TO RELATED APPLICATIONS

This application is a continuation of International Application No. PCT/EP2016/071613 having an international filing date of Sep. 14, 2016 and which claims benefit under 35 U.S.C. § 119 to international application PCT/CN2015/089868 having an international filing date of Sep. 17, 2015. The entire contents of both are incorporated herein by reference.

FIELD OF THE INVENTION

The present invention relates to sulfinylphenyl or sulfonimidoylphenyl benzazepines that are Toll-like Receptor (TLR) agonists, their manufacture, pharmaceutical compositions containing them and their potential use as medicaments. The compounds of formula I may be used for the treatment and prevention (e.g. vaccination) of disorders such as of cancer, autoimmune diseases, inflammation, sepsis, allergy, asthma, graft rejection, graft-versus-host disease, immunodeficiencies, and infectious diseases.

BACKGROUND OF THE INVENTION

The present invention relates to novel sulfinylphenyl or sulfonimidoylphenyl benzazepine compounds having pharmaceutical activity, their manufacture, pharmaceutical compositions containing them and their potential use as medicaments. In particular, the present invention

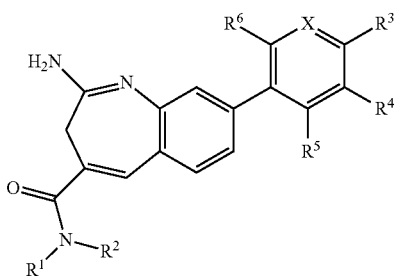

relates to compounds of the formula wherein $R^1$ to $R^6$ and X are as described below, or to pharmaceutically acceptable salts thereof.

Toll-like receptors (TLRs) are a family of membrane-spanning receptors that are expressed on cells of the immune system like dendritic cells, macrophages, monocytes, T cells, B cells, NK cells and mast cells but also on a variety of non-immune cells such as endothelial cells, epithelial cells and even tumor cells (Kawai et al., Immunity, 2011, 34, 637-650, Kawai et al., Nat. Immunol., 2010, 11, 373-384). TLRs that recognize bacterial and fungal components are expressed on the cell surface (i.e. TLR1, 2, 4, 5 and 6), while others that recognize viral or microbial nucleic acids like TLR3, 7, 8 and 9 are localized to the endolysosomal/phagosomal compartment (Henessy et al. Nat. Rev. Drug Discovery 2010, 9, 293-307) and predominantly found to be expressed by cells of the myeloid lineage. TLR ligation leads to activation of NF-κB and IRF-dependent pathways with the specific activation sequence and response with respect to the specific TLR and cell type. While TLR7 is mainly expressed in all dendritic cells subtypes (DC and here highly in pDC, plasmacytoid DC) and can be induced in B cells upon IFNα stimulation (Bekeredjian-Ding et al. J. Immunology 2005, 174:4043-4050), TLR8 expression is rather restricted to monocytes, macrophages and myeloid DC. TLR8 signaling via MyD88 can be activated by bacterial single stranded RNA, small molecule agonists and lately discovered microRNAs (Chen et al. RNA 2013, 19:737-739). The activation of TLR8 results in the production of various pro-inflammatory cytokines such as IL-6, IL-12 and TNF-α as well as enhanced expression of co-stimulatory molecules, such as CD80, CD86, and chemokine receptors (Cros et al. Immunity 2010, 33:375-386). In addition, TLR8 activation can induce type I interferon (IFNβ) in primary human monocytes (Pang et al. BMC Immunology 2011, 12:55).

Small molecule agonists for both the TLR7 and TLR8 receptor as well as analogs modified for use as vaccine adjuvants or conjugates have been identified in many patents (i.e. WO1992015582, WO2007024612, WO2009111337, WO2010093436, WO2011017611, WO2011068233, WO2011139348, WO2012066336, WO2012167081, WO2013033345, WO2013166110, and US2013202629). Clinical experience has been obtained mainly for TLR7 agonists, but only very few clinical studies focused on using highly specific TLR8 agonists. To date, the only FDA (U.S. Food and Drug Administration)-approved small molecule drug is the TLR7 agonist imiquimod (ALDARA™) as a topical agent for the treatment of genital warts, superficial basal cell carcinoma and actinic keratosis. Systemic application however of the early TLR7 agonists like resiquimod has been abandoned due to intolerable cardiotoxicity observed upon global chemokine stimulation at therapeutic levels (Holldack, Drug Discovery Today, 2013, 1-4). Knowledge about TLR8 agonists is less advanced and mostly restricted to data with early mixed TLR7/8 agonists like resiquimod. For the resiquimod agonist, however, the stimulatory capacity of the TLR7 is superior compared to the activation of the TLR8, so that most of the effects of resiquimod are dominated by the effect of TLR7 activity. More recently, TLR8 specific compounds like VTX-2337 have been described by VentiRX Pharmaceuticals (i.e. WO 2007024612), allowing for the first time to analyse the specific role of TLR8 without activation of TLR7 at the same time. At present there is still a need for small molecule TLR8 agonists, specifically those with improved potency or selectivity.

The present invention is directed to benzazepines with improved cellular potency over known TLR8 agonists of this type for use in the treatment of cancer, preferably solid tumors and lymphomas, and for other uses including the treatment of certain skin conditions or diseases, such as atopic dermatitis, the treatment of infectious diseases, preferably viral diseases, and for use as adjuvants in vaccines formulated for use in cancer therapy or by desensitizing of the receptors by continuous stimulation in the treatment of autoimmune diseases.

It has to be noted that these new compounds have improved cellular potency at TLR8 compared to known TLR8 agonists such as VTX-2337. In addition these compounds are highly specific towards TLR8 and possess only low or even no activity towards TLR7. Thus, they are expected to possess advantageous properties compared to combined TLR7/8 agonists due to the more restricted expression pattern of TLR8 resulting in less served side effects when administered systemically.

SUMMARY OF THE INVENTION

The present invention relates to sulfinylphenyl or sulfonimidoylphenyl benzazepine-4-carboxamide compounds of the formula

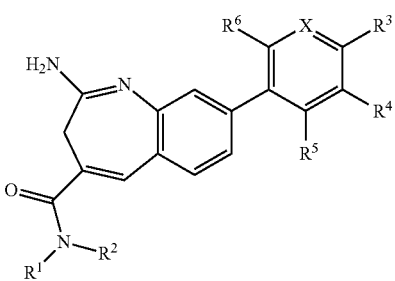

wherein
X is C—$R^7$ or N;
$R^1$ is $C_{3-7}$-alkyl or $C_{3-7}$-cycloalkyl,
$R^2$ is selected from the group consisting of $C_{3-7}$-alkyl, hydroxy-$C_{1-7}$-alkyl, $C_{3-7}$-alkynyl, amino-$C_{1-7}$-alkoxy-$C_{1-7}$-alkoxy-$C_{1-7}$-alkyl, halogen-$C_{1-7}$-alkyl and $C_{3-7}$-cycloalkyl-$C_{1-7}$-alkyl;
one of $R^3$ and $R^4$ is

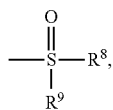

and the other one of $R^3$ and $R^4$ is selected from the group consisting of hydrogen, $C_{1-7}$-alkyl and halogen;
$R^5$, $R^6$ and $R^7$ are independently from each other selected from hydrogen, $C_{1-7}$-alkyl and halogen;
$R^8$ is $C_{1-7}$-alkyl; and
$R^9$ is absent or is =N—$R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl,
or pharmaceutically acceptable salts thereof.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases that can be mediated with TLR agonists, in particular TLR8 agonists. The invention thus relates to a method for the treatment of a disease that can be mediated with TLR agonists such as for example cancer and autoimmune or infectious diseases.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and solvates or salts thereof (e.g., pharmaceutically acceptable salts).

The term "substituent" denotes an atom or a group of atoms replacing a hydrogen atom on the parent molecule.

The term "halogen" refers to fluoro, chloro, bromo and iodo, with fluoro, chloro and bromo being of particular interest. More particularly, halogen refers to fluoro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. More particularly, the term "alkyl" also embraces lower alkyl groups as described below.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl. The term "$C_{2-7}$-alkyl" refers to a straight-chain or branched-chain alkyl group with 2 to 7 carbon atoms as defined above, however the methyl or methylene group is excluded.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl, in particular 2-propenyl (allyl).

The term "lower alkinyl" or "$C_{2-7}$-alkinyl" signifies a straight-chain or branched chain hydrocarbon residue comprising a triple bond and 2 to 7 carbon atoms. Examples of lower alkinyl groups are ethinyl and 1-propinyl (—C≡C=$CH_2$).

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl, 2-methoxyethyl and 2-ethoxyethyl, with 2-ethoxyethyl being of most particular interest.

The term hydroxy or hydroxyl means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower hydroxyalkoxyalkyl" or "hydroxy-$C_{1-7}$-alkoxy-$C_{1-7}$-alkyl" refers to lower alkoxyalkyl groups as defined above wherein at least one of the hydrogen atoms of the lower alkoxy group is replaced by a hydroxy group. Among the lower hydroxyalkoxyalkyl groups of particular interest is 2-hydroxyethoxyethyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl being of more particular interest.

"Amino" refers to the group —$NH_2$. The term "$C_{1-7}$-alkylamino" means a group —NHR, wherein R is lower alkyl and the term "lower alkyl" has the previously given significance. The term "di-$C_{1-7}$-alkylamino" means a group —NRR', wherein R and R' are lower alkyl groups as defined above.

The term "lower aminoalkyl" or "amino-$C_{1-7}$-alkyl" refers to lower alkyl groups as defined above wherein at least one of the hydrogen atoms of the lower alkyl group is replaced by an amino group. Among the particular interesting lower aminoalkyl groups are aminomethyl or 2-aminoethyl.

The term "lower aminoalkoxyalkyl" or "amino-$C_{1-7}$-alkoxy-$C_{1-7}$-alkyl" refers to lower alkoxyalkyl groups as defined above wherein at least one of the hydrogen atoms of the lower alkoxy group is replaced by an amino group. Among the particular interesting lower aminoalkoxyalkyl groups are 2-aminoethoxymethyl or 2-aminoethoxyethyl.

The term "lower aminoalkoxyalkoxyalkyl" or "amino-$C_{1-7}$-alkoxy-$C_{1-7}$-alkoxy-$C_{1-7}$-alkyl" refers to lower alkoxyalkyl groups as defined above wherein at least one of the hydrogen atoms of the lower alkoxy group is replaced by an amino-$C_{1-7}$-alkoxy group. Among the particular interesting lower aminoalkoxyalkoxyalkyl groups are 2-aminoethoxyethoxymethyl or 2-aminoethoxyethoxyethyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to compounds of the formula

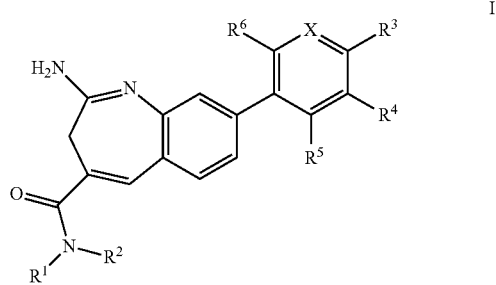

wherein
X is $CR^7$ or N;
$R^1$ is $C_{3-7}$-alkyl or $C_{3-7}$-cycloalkyl,
$R^2$ is selected from the group consisting of $C_{3-7}$-alkyl, hydroxy-$C_{1-7}$-alkyl, $C_{3-7}$-alkinyl, amino-$C_{1-7}$-alkoxy-$C_{1-7}$-alkoxy-$C_{1-7}$-alkyl, halogen-$C_{1-7}$-alkyl and $C_{3-7}$-cycloalkyl-$C_{1-7}$-alkyl;

one of $R^3$ and $R^4$ is

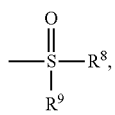

and the other one of $R^3$ and $R^4$ is selected from the group consisting of hydrogen, $C_{1-7}$-alkyl and halogen;
$R^5$, $R^6$ and $R^7$ are independently from each other selected from hydrogen, $C_{1-7}$-alkyl and halogen;
$R^8$ is $C_{1-7}$-alkyl;
$R^9$ is absent or is $=N-R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl,
or pharmaceutically acceptable salts thereof.

In one aspect, the invention relates to compounds of formula I, wherein $R^1$ is $C_{3-7}$-alkyl.

In particular, the invention is concerned with compounds of formula I, wherein $R^1$ is propyl.

In another aspect, the invention refers to compounds of formula I, wherein $R^2$ is $C_{3-7}$-alkyl, more particularly propyl.

Thus, in one aspect, the invention relates to compounds of the formula

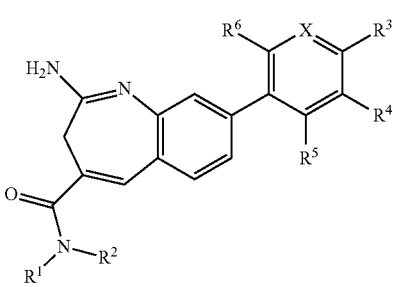

I wherein
X is $CR^7$ or N;
$R^1$ is $C_{3-7}$-alkyl or $C_{3-7}$-cycloalkyl;
$R^2$ is $C_{3-7}$-alkyl;
one of $R^3$ and $R^4$ is

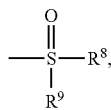

and the other one of $R^3$ and $R^4$ is selected from the group consisting of hydrogen, $C_{1-7}$-alkyl and halogen;
$R^5$, $R^6$ and $R^7$ are independently from each other selected from hydrogen, $C_{1-7}$-alkyl and halogen;
$R^8$ is $C_{1-7}$-alkyl;
$R^9$ is absent or is $=N-R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl,
or pharmaceutically acceptable salts thereof.

In particular, the invention relates to compounds of the formula I, wherein $R^1$ and $R^2$ are $C_{3-7}$-alkyl, in particular propyl, more particularly n-propyl.

In another aspect, the invention refers to compounds of formula I, wherein $R^3$ is selected from the group consisting of hydrogen, $C_{1-7}$-alkyl and halogen and $R^4$ is

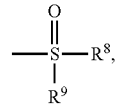

wherein $R^8$ is $C_{1-7}$-alkyl and $R^9$ is absent or is $=N-R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl. In particular, in such compounds $R^3$ is hydrogen.

In a further aspect, the invention relates to compounds of formula I, wherein $R^4$ is selected from the group consisting of hydrogen, $C_{1-7}$-alkyl and halogen and $R^3$ is

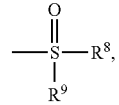

wherein $R^8$ is $C_{1-7}$-alkyl and $R^9$ is absent or is $=N-R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl. More particularly, in such compounds $R^4$ is hydrogen.

In another aspect, the invention refers to compounds of formula I, wherein $R^1$ and $R^2$ are $C_{3-7}$-alkyl, in particular propyl, more particularly n-propyl and wherein $R^3$ is selected from the group consisting of hydrogen, $C_{1-7}$-alkyl and halogen and $R^4$ is

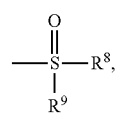

wherein $R^8$ is $C_{1-7}$-alkyl and $R^9$ is absent or is $=N-R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl. In particular, in such compounds $R^3$ is hydrogen. In a subembodiment $R^3$ is hydrogen.

Furthermore, the invention relates to compounds of formula I, wherein $R^5$ and $R^6$ are hydrogen.

In a particular aspect, $R^7$ is hydrogen.

In one aspect, the invention is concerned with compounds of formula I, wherein one of $R^3$ or $R^4$ is

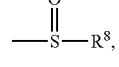

wherein $R^8$ is $C_{1-7}$-alkyl.

Another aspect of the invention relates to compounds of formula I, wherein $R^5$ and $R^6$ are hydrogen and wherein one of $R^3$ or $R^4$ is

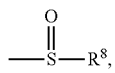

wherein $R^8$ is $C_{1-7}$-alkyl.

In another aspect, the invention relates to compounds of formula I, wherein one of $R^3$ and $R^4$ is

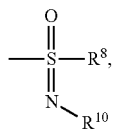

wherein $R^8$ is $C_{1-7}$-alkyl; and $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl.

In a particular aspect, the invention relates to compounds of formula I, wherein $R^{10}$ is hydrogen or hydroxy-$C_{1-7}$-alkoxy-$C_{1-7}$-alkyl.

Another aspect of the invention relates to compounds of formula I, wherein $R^5$ and $R^6$ are hydrogen and wherein one of $R^3$ and $R^4$ is

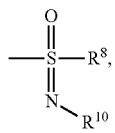

wherein $R^8$ is $C_{1-7}$-alkyl; and $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl. In a a particular aspect $R^{10}$ is hydrogen or hydroxy-$C_{1-7}$-alkoxy-$C_{1-7}$-alkyl.

In another aspect, compounds of formula I of the invention are those, wherein $R^8$ is methyl or ethyl.

In one aspect, the invention relates to compounds of formula I as defined hereinbefore, wherein X is C, meaning compounds of the formula I-a:

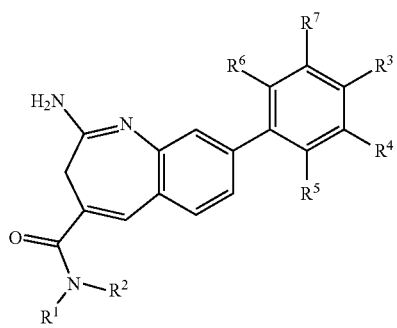

wherein $R^1$ to $R^7$ are as defined herein before.

In another aspect, compounds of formula I are those, wherein X is N, meaning compounds of the formula I-b:

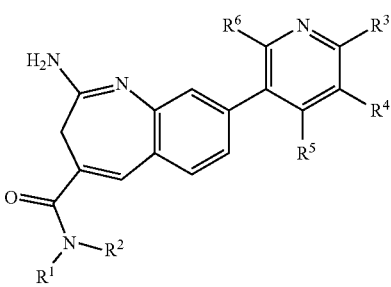

wherein $R^1$ to $R^6$ are as defined herein before.

Particular compounds of formula I according to the invention are the following:

2-amino-8-(4-methylsulfinylphenyl)-N,N-dipropyl-3H-1-benzazepine-4-carboxamide, 2-amino-8-[4-(methylsulfonimidoyl)phenyl]-N,N-dipropyl-3H-1-benzazepine-4-carboxamide, 2-amino-8-[3-[N-[2-(2-hydroxyethoxy)ethyl]-S-methyl-sulfonimidoyl]phenyl]-N,N-dipropyl-3H-1-benzazepine-4-carboxamide, 2-amino-8-(5-methylsulfinyl-3-pyridyl)-N,N-dipropyl-3H-1-benzazepine-4-carboxamide, 2-amino-8-(3-methylsulfinylphenyl)-N,N-dipropyl-3H-1-benzazepine-4-carboxamide, 2-amino-8-[5-(methylsulfonimidoyl)-3-pyridyl]-N,N-dipropyl-3H-1-benzazepine-4-carboxamide, 2-amino-8-[3-(methylsulfonimidoyl)phenyl]-N,N-dipropyl-3H-1-benzazepine-4-carboxamide, 2-amino-8-(4-ethylsulfinylphenyl)-N,N-dipropyl-3H-1-benzazepine-4-carboxamide, 2-amino-8-[4-(ethylsulfonimidoyl)phenyl]-N,N-dipropyl-3H-1-benzazepine-4-carboxamide, 2-amino-8-(3-ethylsulfinylphenyl)-N,N-dipropyl-3H-1-benzazepine-4-carboxamide, 2-amino-8-[3-(ethylsulfonimidoyl)phenyl]-N,N-dipropyl-3H-1-benzazepine-4-carboxamide, and pharmaceutically acceptable salts thereof.

More particularly, the invention relates to the following compounds of formula I:

2-amino-8-(5-methylsulfinyl-3-pyridyl)-N,N-dipropyl-3H-1-benzazepine-4-carboxamide, 2-amino-8-(3-methylsulfinylphenyl)-N,N-dipropyl-3H-1-benzazepine-4-carboxamide, 2-amino-8-(3-ethylsulfinylphenyl)-N,N-dipropyl-3H-1-benzazepine-4-carboxamide, and pharmaceutically acceptable salts thereof.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

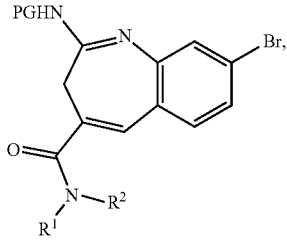

wherein R¹ and R² are as defined herein before and PG is a protecting group, with bis(pinacolato)diboron under basic conditions in the presence of a Pd catalyst to obtain a boronic ester of the formula III

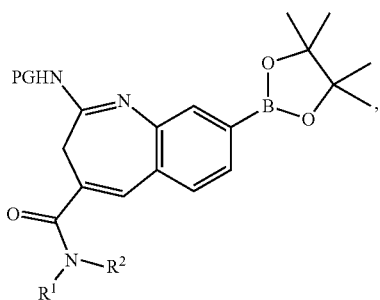

wherein R¹ and R² are as defined herein before and PG is a protecting group, and coupling the compound III under basic conditions in the presence of a Pd catalyst with a bromide of the formula

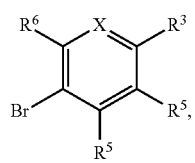

wherein R³ to R⁶ and X are as defined herein before, and removing the protecting group PG under acidic conditions to obtain a compound of the formula I

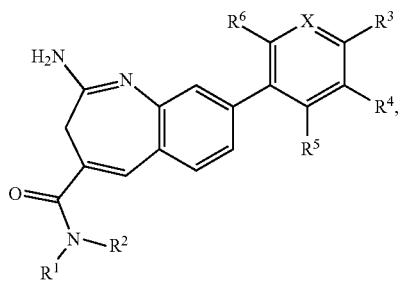

wherein R¹ to R⁶ and X are as defined herein before, and, if desired, converting the compound obtained into a pharmaceutically acceptable salt.

In particular, a suitable protecting group PG is an amino-protecting group selected from Boc (tert-butoxycarbonyl), benzyl (Bz) and benzyloxycarbonyl (Cbz). In particular, the protecting group is Boc.

"Removing the protecting group PG under acidic conditions" means treating the protected compound with acids in a suitable solvent, for instance trifluoroacetic acid (TFA) in a solvent such as dichloromethane (DCM) can be employed.

Under "basic conditions" means the presence of a base, in particular a base selected from the group consisting of sodium carbonate, potassium carbonate, caesium carbonate, potassium phosphate and sodium hydroxide. Typical solvents are selected from the group consisting of 1.4-dioxane, toluene, THF, dimethylformamide and mixtures of water and organic solvents.

The term "Pd catalyst" refers to any Pd(0) catalyst that is appropriate to be used in a Suzuki coupling. Examples for a Pd catalyst appropriate for the Suzuki coupling are selected from the group consisting of $Pd(PPh_3)_4$, $PdCl_2(PPh_3)_2$ and $Pd(dppf)_2Cl_2$.

The invention further relates to compounds of formula I as defined above obtainable according to a process as defined above.

The compounds of the present invention can be prepared by any conventional means. Suitable processes for synthesizing these compounds as well as their starting materials are provided in the schemes below and in the examples. All substituents, in particular, R¹ to R⁶ and Y are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compounds of formula I is shown in Scheme 1 below.

Scheme 1

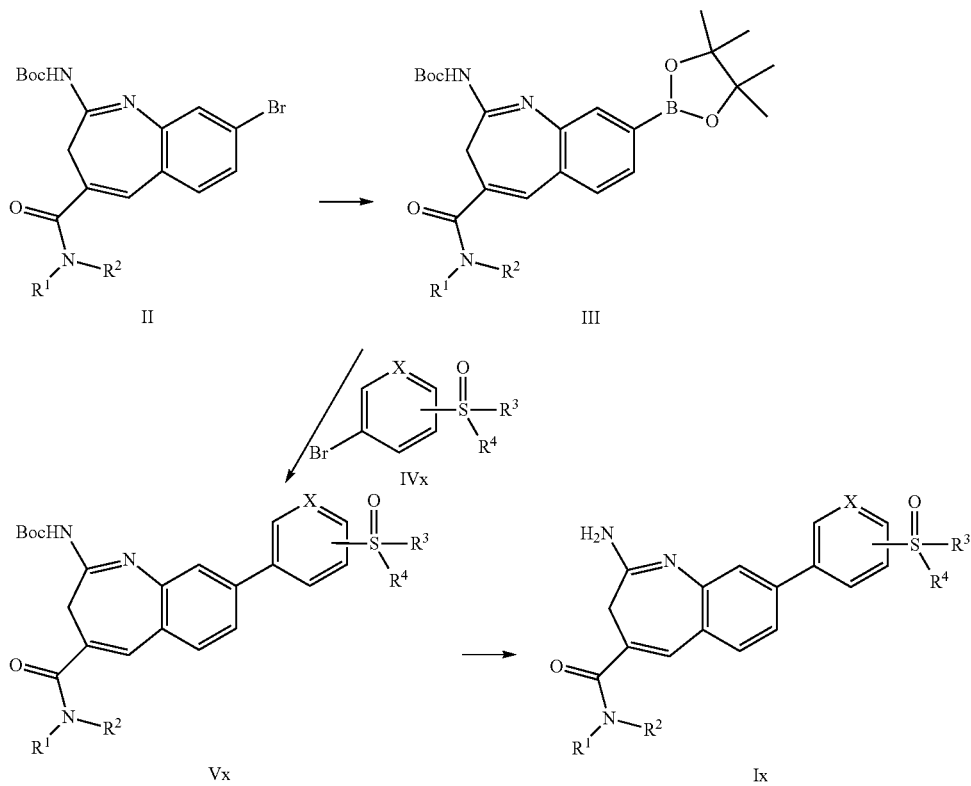

A compound of formula I can be prepared according to Scheme 1. Palladium catalyzed transformation of aryl bromide II gives aryl boronic acid ester III. A Suzuki coupling between boronic acid pinacol ester III and a selected aryl bromide or heteroaryl bromide IVx gives compound Vx. Boc deprotection of compound Vx under acidic conditions gives a compound of formula Ix.

Boronic acid pinacol ester III can be prepared by reacting bromide II with bis(pinacolato)diboron and Pd(dppf)$_2$Cl$_2$ under nitrogen atmosphere and at elevated temperatures. The reaction is typically running for several hours in a solvent like 1,4-dioxane to give compound III after chromatographic purification.

The boronic acid pinacol ester III is further reacted with another selected aryl bromide or heteroaryl bromide IVx using typical Suzuki coupling conditions (catalytic Pd(dppf)$_2$Cl$_2$, sodium carbonate and elevated temperatures) under nitrogen atmosphere for several hours. Compound Vx is obtained after chromatographic purification.

A compound of formula I can be prepared by Boc deprotection of compound Vx with TFA in dichloromethane and subsequent purification by prep-HPLC.

If one of the starting materials contains one or more functional groups which are not stable or are reactive under the reaction conditions of one or more reaction steps, appropriate protecting groups (PG) (as described e.g. in T. W. Greene et al., Protective Groups in Organic Chemistry, John Wiley and Sons Inc. New York 1999, 3rd edition) can be introduced before the critical step applying methods well known in the art. Such protecting groups can be removed at a later stage of the synthesis using standard methods known in the art.

If one or more compounds of the formula contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

As described herein before, the compounds of formula I of the present invention can be used as medicaments for the treatment of diseases which are mediated by TLR agonists, in particular for the treatment of diseases which are mediated by TLR8 agonists.

The compounds defined in the present invention are agonists of TLR8 receptors in cellular assays in vitro. Accordingly, the compounds of the present invention are expected to be potentially useful agents in the treatment of diseases or medical conditions that may benefit from the activation of the immune system via TLR8 agonists. They are useful in the treatment or prevention of diseases such as cancer, autoimmune diseases, inflammation, sepsis, allergy, asthma, graft rejection, graft-versus-host disease, immunodeficiencies, and infectious diseases.

In more detail, the compounds of formula I of the present invention are useful in oncology, i.e. they may be used in the treatment of common cancers including bladder cancer, head and neck cancer, prostate cancer, colorectal cancer, kidney cancer, breast cancer, lung cancer, ovarian cancer, cervical cancer, liver cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The compounds of formula I of the present invention are also useful in the treatment of autoimmune diseases. An "autoimmune disease" is a disease or disorder arising from and directed against an individual's own tissues or organs or a co-segregate or manifestation thereof or resulting condition therefrom. "Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). In a particular aspect, the autoimmune disease is associated with the skin, muscle tissue, and/or connective tissue.

Particular autoimmune diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases, ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)), allergic conditions and responses, food allergies, drug allergies, insect allergies, rare allergic disorders such as mastocytosis, allergic reaction, eczema including allergic or atopic eczema, asthma such as bronchial asthma and auto-immune asthma, conditions involving infiltration of myeloid cells and T cells and chronic inflammatory responses:

The compounds of formula I of the present invention are also useful in the treatment of infectious diseases. Thus, they may be useful in the treatment of viral diseases, in particular for diseases caused by infection with viruses selected from the group consisting of papilloma viruses, such as human papilloma virus (HPV) and those that cause genital warts, common warts and plantar warts, herpes simplex virus (HSV), molluscum contagiosum, hepatitis B virus (HBV), hepatitis C virus (HCV), Dengue virus, variola virus, human immunodeficiency virus (HIV), cytomegalovirus (CMV), varicella zoster virus (VZV), rhinovirus, enterovirus, adenovirus, coronavirus (e.g. SARS), influenza, mumps and parainfluenza.

They may also be useful in the treatment of bacterial diseases, in particular for diseases caused by infection with bacteria selected from the group consisting of *mycobacterium* such as *mycobacterium tuberculosis, mycobacterium avium* and *mycobacterium leprae*. The compounds of formula I of the present invention may further be useful in the treatment of other infectious diseases, such as *chlamydia*, fungal diseases, in particular fungal diseases selected from the group consisting of candidiasis, aspergillosis and cryptococcal meningitis, and parasitic diseases such as *Pneumocystis carnii*, pneumonia, cryptosporidiosis, histoplasmosis, toxoplasmosis, trypanosome infection and leishmaniasis.

Thus, the expression "diseases which are mediated by TLR agonists" means diseases which may be treated by activation of the immune system with TLR8 agonists such as cancer, autoimmune diseases, inflammation, sepsis, allergy, asthma, graft rejection, graft-versus-host disease, immunodeficiencies, and infectious diseases. In particular, the expression "diseases which are mediated by TLR agonists" means cancer, autoimmune diseases, inflammation, sepsis, allergy, asthma, graft rejection, graft-versus-host disease, immunodeficiencies, and infectious diseases.

In a particular aspect, the expression "which are mediated by TLR agonists" relates to cancer selected from the group consisting of bladder cancer, head and neck cancer, liver cancer, prostate cancer, colorectal cancer, kidney cancer, breast cancer, lung cancer, ovarian cancer, cervical cancer, pancreatic cancer, bowel and colon cancer, stomach cancer, thyroid cancer, melanoma, skin and brain tumors and malignancies affecting the bone marrow such as leukemias and lymphoproliferative systems, such as Hodgkin's and non-Hodgkin's lymphoma; including the prevention (e.g. vaccination) and treatment of metastatic cancer and tumor recurrences, and paraneoplastic syndromes.

The invention also relates to pharmaceutical compositions comprising a compound of formula I as defined above and a pharmaceutically acceptable carrier and/or adjuvant. More specifically, the invention relates to pharmaceutical compositions useful for the treatment of diseases which are which are mediated by TLR agonists.

Further, the invention relates to compounds of formula I as defined above for use as therapeutically active substances, particularly as therapeutically active substances for the treatment of diseases which are which are mediated by TLR agonists. In particular, the invention relates to compounds of formula I for use in the treatment of cancers or autoimmune diseases or infectious diseases selected from the group consisting of viral diseases, bacterial diseases, fungal diseases and parasitic diseases.

In another aspect, the invention relates to a method for the treatment a of diseases which are mediated by TLR agonists, which method comprises administering a therapeutically active amount of a compound of formula I to a human being or animal. In particular, the invention relates to a method for the treatment of cancers and infectious diseases selected from the group consisting of viral diseases, bacterial diseases, fungal diseases and parasitic diseases.

The invention further relates to the use of compounds of formula I as defined above for the treatment of diseases which are mediated by TLR agonists.

In addition, the invention relates to the use of compounds of formula I as defined above for the preparation of medicaments for the treatment of diseases which are mediated by TLR agonists. In particular, the invention relates to the use of compounds of formula I as defined above for the preparation of medicaments for the treatment of cancers or autoimmune diseases or infectious diseases selected from the group consisting of viral diseases, bacterial diseases, fungal diseases and parasitic diseases.

In a further aspect, compounds of formula I can be in combination with one or more additional treatment modalities in a regimen for the treatment of cancer.

Combination therapy encompasses, in addition to the administration of a compound of the invention, the adjunctive use of one or more modalities that are effective in the treatment of cancer. Such modalities include, but are not limited to, chemotherapeutic agents, immunotherapeutics, anti-angiogenic agents, cytokines, hormones, antibodies, polynucleotides, radiation and photodynamic therapeutic agents. In a specific aspect, combination therapy can be used to prevent the recurrence of cancer, inhibit metastasis, or inhibit the growth and/or spread of cancer or metastasis. As used herein, "in combination with" means that the compound of formula I is administered as part of a treatment regimen that comprises one or more additional treatment modalities as mentioned above. The invention thus also relates to a method for the treatment of cancer, which method comprises administering a therapeutically active amount of a compound of formula I in combination with one or more other pharmaceutically active compounds to a human being or animal.

Compounds of formula I can be used alone or in combination with one or more additional treatment modalities in treating autoimmune diseases.

Combination therapy encompasses, in addition to the administration of a compound of the invention, the adjunctive use of one or more modalities that aid in the prevention or treatment of autoimmune diseases. Such modalities include, but are not limited to, chemotherapeutic agents, immunotherapeutics, anti-angiogenic agents, cytokines, hormones, antibodies, polynucleotides, radiation and photodynamic therapeutic agents. As used herein, "in combination with" means that the compound of formula I is administered as part of a treatment regimen that comprises one or more additional treatment modalities as mentioned above. The invention thus also relates to a method for the treatment of autoimmune diseases, which method comprises administering a therapeutically active amount of a compound of formula I in combination with one or more other pharmaceutically active compounds to a human being or animal.

In a further aspect, compounds of formula I can be used alone or in combination with one or more additional treatment modalities in treating infectious diseases.

Combination therapy encompasses, in addition to the administration of a compound of the invention, the adjunctive use of one or more modalities that aid in the prevention or treatment of infectious diseases. Such modalities include, but are not limited to, antiviral agents, antibiotics, and anti-fungal agents. As used herein, "in combination with" means that the compound of formula I is administered as part of a treatment regimen that comprises one or more additional treatment modalities as mentioned above. The invention thus also relates to a method for the treatment of infectious diseases, which method comprises administering a therapeutically active amount of a compound of formula I in combination with one or more other pharmaceutically active compounds to a human being or animal.

Pharmacological Test

The following tests were carried out in order to determine the activity of the compounds of formula I:

For TLR8 and TLR7 activity testing, HEK-Blue human TLR8 or TLR7 cells (Invivogen, San Diego, Calif., USA) are used, respectively. These cells are designed for studying the stimulation of human TLR8 or TLR7 by monitoring the activation of NF-κB. A SEAP (secreted embryonic alkaline phosphatase) reporter gene is placed under the control of the IFN-b minimal promoter fused to five NF-κB and AP-1-binding sites. Therefore the reporter expression is regulated by the NF-κB promoter upon stimulation of human TLR8 or TLR7 for 20 hours. The cell culture supernatant SEAP reporter activity was determined using Quanti Blue kit (Invivogen, San Diego, Ca, USA) at a wavelength of 640 nm, a detection medium that turns purple/blue in the presence of alkaline phosphatase.

The compounds according to formula I have an activity ($EC_{50}$ value) in the above assay for human TLR8 in the range of 0.01 nM to 0.1 µM, more particularly of 0.01 nM to 0.03 µM, whereas the activity ($EC_{50}$ value) in the above assay for human TLR7 is greater than 1 µM, in the range of 2 µM to >100 µM, meaning the compounds show high selectivity towards human TLR8.

For example, the following compounds showed the following $EC_{50}$ values in the assay described above:

| Example | human TLR8 $EC_{50}$ [µM] | human TLR7 $EC_{50}$ [µM] |
|---|---|---|
| 1 | 0.026 | 19 |
| 2 | 0.025 | 25 |
| 3 | 0.011 | 55 |
| 4 | 0.008 | 2.4 |
| 5 | 0.004 | 12.1 |
| 6 | 0.028 | 14.8 |
| 7 | 0.013 | 15.4 |
| 8 | 0.021 | 23 |
| 9 | 0.025 | 32 |
| 10 | 0.008 | 16 |
| 11 | 0.015 | 39 |

Pharmaceutical Compositions

The compounds of formula I and their pharmaceutically acceptable salts can be used as medicaments, e.g., in the form of pharmaceutical preparations for enteral, parenteral or topical administration. The compounds of formula I and their pharmaceutically acceptable salts may be administered by systemic (e.g., parenteral) or local (e.g., topical or intralesional injection) administration. In some instances, the pharmaceutical formulation is topically, parenterally, orally, vaginally, intrauterine, intranasal, or by inhalation administered. As described herein, certain tissues may be preferred targets for the TLR agonist. Thus, administration of the TLR agonist to lymph nodes, spleen, bone marrow, blood, as well as tissue exposed to virus, are preferred sites of administration.

In one aspect, the pharmaceutical formulation comprising the compounds of formula I or its pharmaceutically acceptable salts is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used. Formulations of the compounds of formula I suitable for parenteral administration are generally formulated in USP water or water for injection and may further comprise pH buffers, salts bulking agents, preservatives, and other pharmaceutically acceptable excipients.

Transdermal administration is accomplished by application of a cream, rinse, gel, etc. capable of allowing the TLR agonist to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Administration via the transdermal and transmucosal routes may be continuous or pulsatile.

Pulmonary administration is accomplished by inhalation, and includes delivery routes such as intranasal, transbronchial and transalveolar routes. Formulations of compounds of formula I suitable for administration by inhalation including, but not limited to, liquid suspensions for forming aerosols as well as powder forms for dry powder inhalation delivery systems are provided. Devices suitable for administration by inhalation include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

The compounds of formula I and pharmaceutically acceptable salts thereof may also be administered orally, e.g., in the form of tablets, coated tablets, dragées, hard and soft gelatine capsules.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example C2

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
| --- | --- |
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The following examples serve to illustrate the present invention in more detail. They are, however, not intended to limit its scope in any manner.

EXAMPLES

Abbreviations Used Therein:

Boc$_2$O=di-tert-butyl dicarbonate, Boc=t-butyl carbamate, CD$_3$OD=deuterated methanol, d=day, DIPEA=N,N-diisopropylethylamine, DCM=dichloromethane, DMAP: 4-dimethylaminopyridine, DMF-DMA: N,N-dimethylformamide dimethyl acetal, EA=ethylacetate or EtOAc, Eaton's regent: 7.7 wt % phosphorus pentoxide solution in methanesulfonic acid, m-CPBA: meta-Chloroperoxybenzoic acid, EC$_{50}$=half maximal effective concentration, EDCI=1-(3-Dimethylaminopropyl)-3-ethylcarbodiimide hydrochloride, h or hr=hour, HOBT=N-hydroxybenzotriazole, HPLC=high performance liquid chromatography, HPLC-UV=high performance liquid chromatography with ultraviolet detector, Hz=hertz, mg=milligram, MHz=megahertz, min=minute(s), mL=milliliter, mm=millimeter, mM=mmol/L, mmol=millimole, MS=mass spectrometry, MW=molecular weight, NMR=nuclear magnetic resonance, PE=petroleum ether, prep-HPLC=preparative high performance liquid chromatography, rt=room temperature, sat.=saturated, TEA=triethylamine, TFA=trifluoroacetic acid, THF=tetrahydrofuran, μM=micromole, μm=micrometer, UV=ultraviolet detector, OD=optical density, Pd(dppf)$_2$Cl$_2$=[1,1'-Bis(diphenylphosphino)-ferrocene]dichloropalladium (II), TLR8=toll-like receptor 8, TLR7=toll-like receptor 7, NF-κB=nuclear factor kappa-light-chain-enhancer of activated B cells, SEAP=secreted embryonic alkaline phosphatase, IFN-β=interferon-beta.

Example A—Preparation of Key Intermediate G tert-Butyl N-[8-bromo-4-(dipropylcarbamoyl)-3H-1-benzazepin-2-yl]carbamate A detailed synthetic route is provided in Scheme 2.

Scheme 2

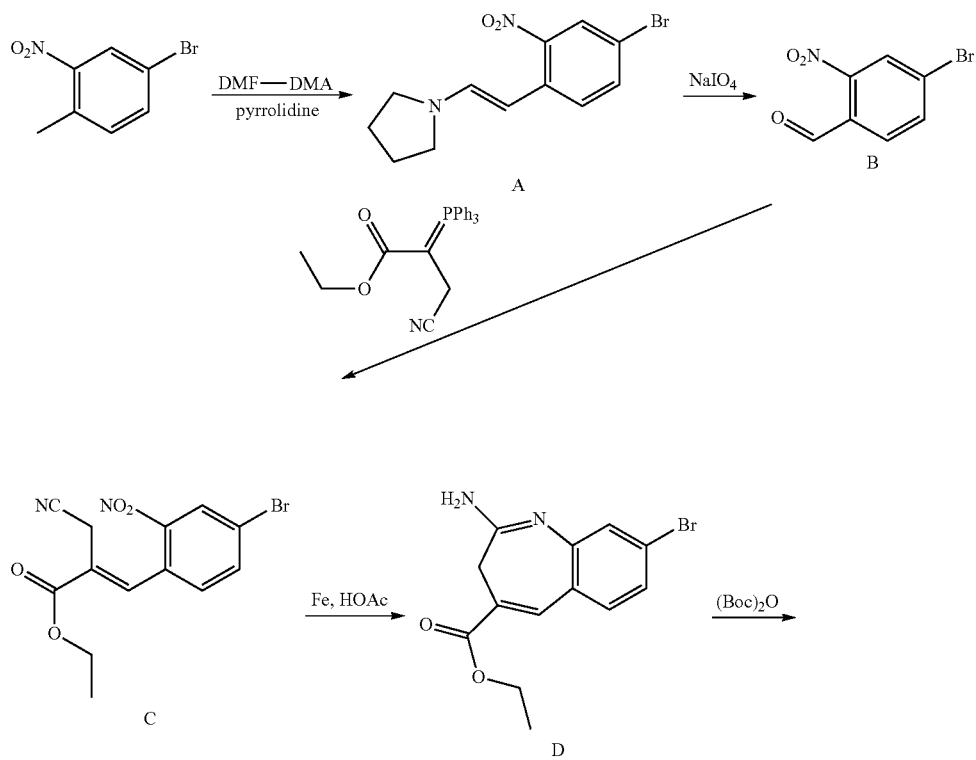

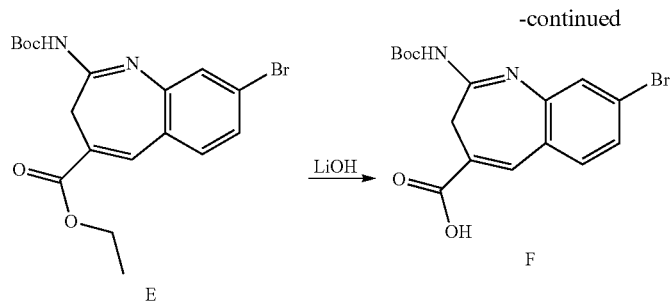
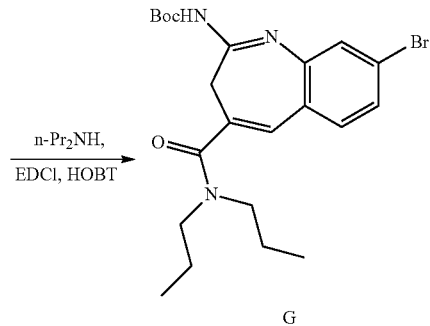

a) Preparation of Compound A:

To a solution of 4-bromo-1-methyl-2-nitro-benzene (100 g, 0.46 mol) in DMF (1 L) was added successively pyrrolidine (39.6 g, 0.59 mol) and DMF-DMA (70 g, 0.59 mol). After the reaction mixture was stirred at 100° C. for 4 hours, the solvent was concentrated under reduced pressure to give 1-[(E)-2-(4-bromo-2-nitro-phenyl)vinyl]pyrrolidine (compound A, 137 g, crude) as brown oil which was used directly in the next step. MS: m/z=297 (M+H)+.

b) Preparation of Compound B:

To a solution of 1-[(E)-2-(4-bromo-2-nitro-phenyl)vinyl]pyrrolidine (compound A, 137 g, 0.47 mol, crude) in a mixed solvent of THF (1.7 L) and water (2.0 L) was added NaIO$_4$ (298 g, 1.40 mol) in portions at 10° C. After the reaction mixture was stirred at 25° C. for 20 hours, it was filtered and the filtrate was extracted with EA (3 L). The separated organic layer was washed with brine, dried over anhydrous Na$_2$SO$_4$, filtered and concentrated to give the crude product. The crude product was purified by silica gel column chromatography using 5% ethyl acetate in PE to give 4-bromo-2-nitro-benzaldehyde (compound B, 66 g, 61%) as a yellow solid. MS: m/z=230 (M+H)+.

c) Preparation of Compound C:

To a solution of 4-bromo-2-nitro-benzaldehyde (compound B, 65 g, 0.28 mol) in toluene (700 mL) was added ethyl 3-cyano-2-(triphenyl phosphoranylidene) propionate (120 g, 0.31 mol) at 25° C. After the reaction was stirred at 25° C. for 18 hours, the reaction mixture was concentrated. Then methanol (500 mL) was added. After the solution was kept in refrigerator for 4 hours, a precipitate was formed and collected by filtration to give 2-[1-(4-bromo-2-nitro-phenyl)-(E)-methylidene]-3-cyano-propionic acid ethyl ester (compound C, 75 g, 78%) as a white solid. MS: m/z=298 (M+H)+.

d) Preparation of Compound D:

To a stirred solution of 2-[1-(4-bromo-2-nitro-phenyl)-meth-(E)-ylidene]-3-cyano-propionic acid ethyl ester (compound C, 75 g, 0.22 mol) in AcOH (1.1 L) was added Fe (74 g, 1.33 mol) at 80° C. After the reaction mixture was heated at 80° C. for 3 hours, the reaction mixture was filtered off through a celite pad. The celite pad was washed with acetic acid. The combined filtrates were concentrated in vacuo and the residue was basified with saturated NaHCO$_3$ (300 mL). Ethyl acetate (1 L) was then added and the mixture was stirred for 10 mins. The undissolved material was further filtered off through a celite pad. The celite pad was washed with ethyl acetate (800 mL). After phase separation, the organic layer was collected and washed with water, dried over Na$_2$SO$_4$ and concentrated in vacuo to give the crude product. The crude product was further rinsed with diethyl ether (100 mL) to give ethyl 2-amino-8-bromo-3H-1-benzazepine-4-carboxylate (compound D, 50 g, 73%) as a light yellow solid. MS: m/z=309 (M+H)+.

e) Preparation of Compound E:

To a solution of ethyl 2-amino-8-bromo-3H-1-benzazepine-4-carboxylate (compound D, 50 g, 0.16 mol) and TEA (26.1 g, 0.26 mol) in DCM (500 mL) was added a solution of Boc$_2$O (56.6 g, 0.26 mol) in DCM (100 mL) at 0-5° C. After the reaction was stirred at 25° C. for 42 hours, water (200 mL) was added. The organic layer was separated, washed with brine, dried over Na$_2$SO$_4$, filtered and concentrated. The residue was slurried in EA and PE and filtered to give ethyl 8-bromo-2-(tert-butoxycarbonylamino)-3H-1-benzazepine-4-carboxylate (compound E, 57 g, 86%) as a yellow solid. MS: m/z=409 (M+H)+.

f) Preparation of Compound F:

To a solution of ethyl 8-bromo-2-(tert-butoxycarbonylamino)-3H-1-benzazepine-4-carboxylate (compound E, 10 g, 24.5 mmol) in THF (60 mL) was added LiOH (37 mL, 1M) in a mixed solvent of EtOH (18 mL) and water (18 mL). The reaction mixture was stirred at 25° C. for 18 hours. A solution of LiOH (10 mL, 1M) in EtOH (5 mL) and water (5 mL) was added, and the reaction mixture was further stirred at 25° C. for 5 hours. After the reaction mixture was acidified to pH=5 with 10% citric acid, it was extracted with EA (50 mL×3). The organic layers were combined, dried over anhydrous Na$_2$SO$_4$, filtered, and concentrated to give 8-bromo-2-(tert-butoxycarbonylamino)-3H-1-benzazepine-4-carboxylic acid (compound F, 9.6 g, crude) as a yellow solid. MS: m/z=380 (M+H)+.

g) Preparation of Compound G:

To a solution of 8-bromo-2-(tert-butoxycarbonylamino)-3H-1-benzazepine-4-carboxylic acid (compound F, 9.6 g, 25.3 mmol) in DCM (360 mL) was successively added EDCI (12 g, 63.1 mmol), HOBT (4.1 g, 30.3 mmol), DIPEA (13 g, 101 mmol) and DMAP (770 mg, 6.3 mmol) at 10° C. After the reaction mixture was stirred for 30 mins at 25° C., N-propylpropan-1-amine (3.8 g, 37.9 mmol) was added. The reaction mixture was stirred at 25° C. for 3 hours. Water was then added and the mixture was extracted with DCM, dried over Na$_2$SO$_4$ and concentrated in vacuo. The residue was purified by silica gel chromatography (PE:EA=5:1) to give tert-butyl N-[8-bromo-4-(dipropylcarbamoyl)-3H-1-benzazepin-2-yl]carbamate (compound G, 8.6 g, 73%) as a yellow solid. 1H NMR (300 MHz, DMSO-d6): δ ppm=10.25-10.07 (m, 1H), 7.44-7.24 (m, 3H), 6.86-6.79 (m, 1H), 3.28-3.14 (m, 4H), 3.13-3.01 (m, 2H), 1.62-1.45 (m, 4H), 1.43 (s, 9H), 1.00-0.62 (m, 6H). MS: m/z=464 (M+H)+.

Example 1

2-Amino-8-(4-methylsulfinylphenyl)-N,N-dipropyl-3H-1-benzazepine-4-carboxamide

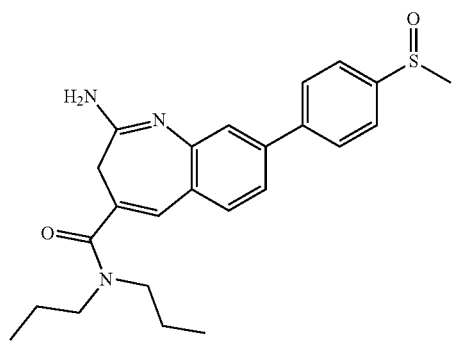 [SMILES: CCCN(CCC)C(=O)C1=Cc2ccc(-c3ccc(S(C)=O)cc3)cc2N=C(N)C1]

The title compound was prepared according to the general synthetic route shown in Scheme 1. A detailed synthetic route is provided in Scheme 3.

Scheme 3:

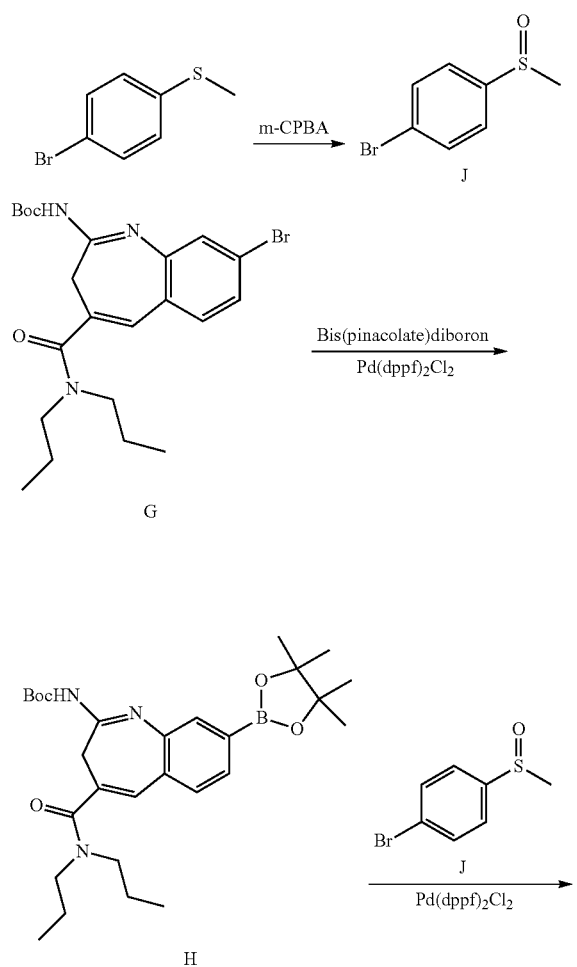

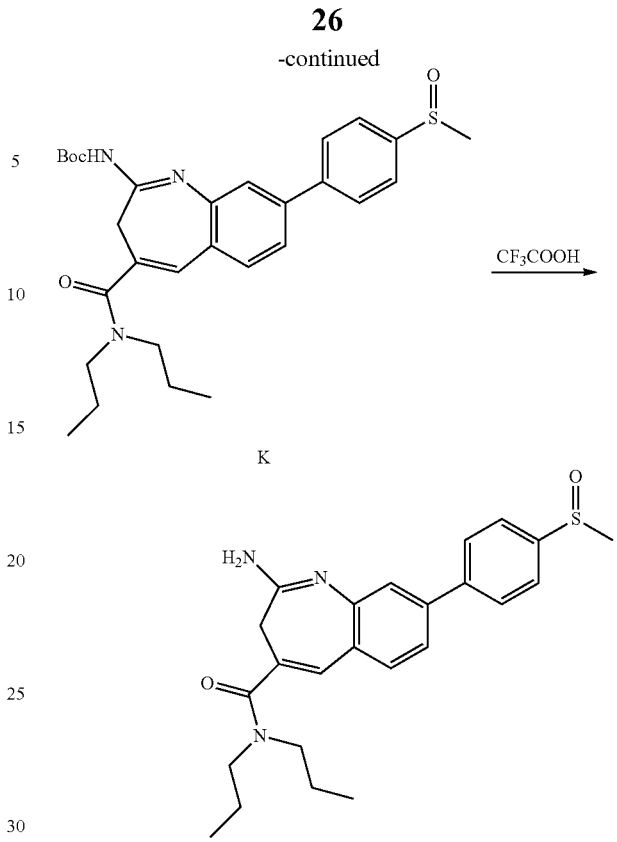

Example 1

Step 1: Preparation of Compound J

To a solution of 1-bromo-4-methylsulfanyl-benzene (4.99 g, 24.6 mmol) in DCM (75 ml) was added meta-chloroperoxybenzoic acid (5.57 g, 25.8 mmol) at 0° C. After the reaction mixture was stirred at 20° C. for 18 hours, it was quenched with aq. $Na_2SO_3$ (30 mL) and aq. $NaHCO_3$ (30 mL). The organic layer was separated, washed with brine, dried over anhydrous $Na_2SO_4$ and concentrated in vacuo to give a residue. The residue was purified by trituration (EA:PE=10 mL, 1:9) to give the desired product 1-bromo-4-(methylsulfinyl)benzene (compound J, 4.8 g, 77.4%) as a white solid. MS: calc'd 219 $(M+H)^+$, measured 219 $(M+H)^+$.

Step 2: Preparation of Compound H

To a stirred solution of tert-butyl N-[8-bromo-4-(dipropylcarbamoyl)-3H-1-benzazepin-2-yl]carbamate (compound G, 5.0 g, 10.7 mmol) in 1,4-dioxane (100 mL) was added bis(pinacolato)diborone (3.0 g, 11.8 mmol), potassium acetate (2.1 g, 21.4 mmol) and $Pd(dppf)Cl_2$ (787 mg, 1.0 mmol) under nitrogen atmosphere. After the reaction mixture was stirred at 90° C. for 3 hours, water was added. The solution was extracted with EA and concentrated in vacuo. The residue was purified by flash-HPLC to give tert-butyl N-[4-(dipropylcarbamoyl)-8-(4,4,5,5-tetramethyl-1,3,2-dioxaborolan-2-yl)-3H-1-benzazepin-2-yl]carbamate (compound H, 3.5 g, 64%) as a yellow solid. MS: m/z=512 $(M+H)^+$, measured 512 $(M+H)^+$.

Step 3: Preparation of Compound K

To a solution of tert-butyl N-[4-(dipropylcarbamoyl)-8-(4,4,5,5-tetramethyl-1,3,2-dioxaborolan-2-yl)-3H-1-benzazepin-2-yl]carbamate (compound H, 400 mg, 0.78 mmol) in 1,4-dioxane (10 mL) was added 1-bromo-4-methylsulfinyl-benzene (compound I, 187 mg, 0.86 mmol), sodium carbonate (207 mg, 1.96 mmol), water (2 mL) and Pd(dppf)

Cl₂ (57 mg, 0.078 mmol) under nitrogen atmosphere. After the reaction mixture was stirred at 50° C. for 18 hours, the undissolved material was filtered. The filtrate was diluted with water (10 mL) and EtOAc (20 mL). The organic layer was separated, dried over Na₂SO₄ and concentrated to give the crude product. The crude product was purified by flash-HPLC to give tert-butyl (4-(dipropylcarbamoyl)-8-(4-(methylsulfinyl)phenyl)-3H-benzo[b]azepin-2-yl)carbamate (compound K, 150 mg, 37%). MS: calc'd 524 (M+H)+, measured 524 (M+H)+.

Step 4: Preparation of Example 1

To a solution of tert-butyl N-[4-(dipropylcarbamoyl)-8-(4-methylsulfinylphenyl)-3H-1-benzazepin-2-yl]carbamate (compound J, 150 mg) in DCM (2 mL) was added TFA (0.5 mL) in DCM (0.5 mL) at 0° C. After the reaction mixture was stirred at 25° C. for 1.5 hours, solvent was removed and the residue was purified by prep-HPLC to give 2-amino-N,N-dipropyl-8-(4-methylsulfinylphenyl)-3H-1-benzazepine-4-carboxamide (Example 1) as a white solid (22 mg). 1H NMR (METHANOL-d4, 400 MHz) δ ppm=7.99-7.93 (m, 2H), 7.90-7.84 (m, 2H), 7.80-7.75 (m, 1H), 7.73-7.66 (m, 2H), 7.13-7.09 (m, 1H), 3.57-3.43 (m, 4H), 3.40-3.37 (m, 2H), 2.88 (s, 3H), 1.79-1.64 (m, 4H), 1.10-0.84 (m, 6H). MS: calc'd 424 (M+H)⁺, measured 424 (M+H)⁺.

Example 2

2-Amino-8-[4-(methylsulfonimidoyl)phenyl]-N,N-dipropyl-3H-1-benzazepine-4-carboxamide

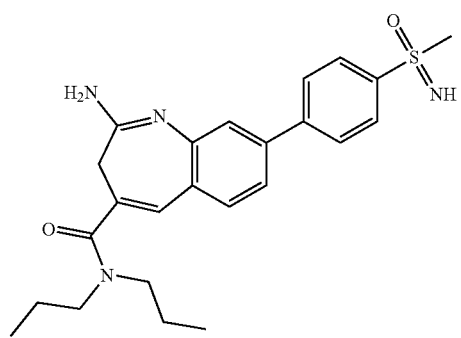 [SMILES: CCCN(CCC)C(=O)C1=Cc2ccc(-c3ccc(S(C)(=N)=O)cc3)cc2N=C(N)C1]

The title compound was prepared according to the general synthetic routes shown in Scheme 1. A detailed synthetic route is provided in Scheme 4.

Scheme 4:

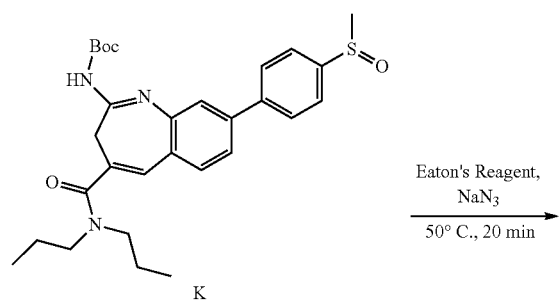

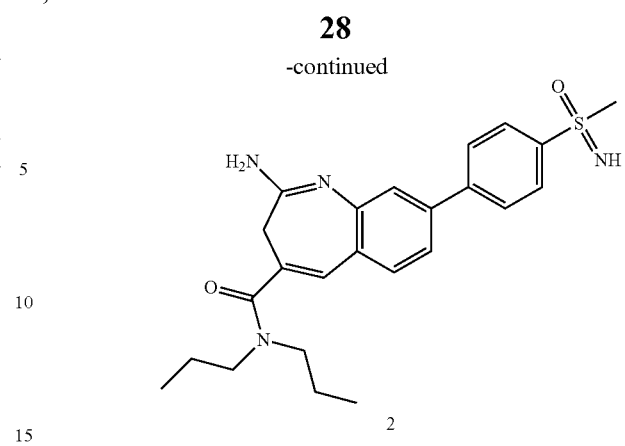

To a solution of tert-butyl (4-(dipropylcarbamoyl)-8-(4-(methylsulfinyl)phenyl)-3H-benzo[b]azepin-2-yl)carbamate (Compound J, 150.0 mg, 0.28 mmol) in Eaton's regent (1.5 mL) was added NaN₃ (55.8 mg, 0.86 mmol). After the reaction mixture was stirred at 50° C. for 20 min, it was poured into 1 M ammonium hydroxide solution at 0° C. The mixture was extracted with DCM (30 mL×2). The organic layer was washed with brine, dried over anhydrous Na₂SO₄, filtered and purified by prep-HPLC to give 2-amino-8-[4-(methylsulfonimidoyl)phenyl]-N,N-dipropyl-3H-1-benzazepine-4-carboxamide (Example 2, 18.0 mg) as a white solid. 1H NMR (METHANOL-d4, 400 MHz) δ ppm=8.12-8.09 (m, 2H), 7.94-7.92 (m, 2H), 7.49-7.42 (m, 3H), 6.91 (s, 1H), 3.47-3.44 (m, 4H), 3.3 (s, 2H), 2.91 (s, 3H), 1.71-1.69 (m, 4H), 0.92 (m, 6H). MS: calc'd 439 (M+H)+, measured 439 (M+H)+.

Example 3

2-Amino-8-[3-[N-[2-(2-hydroxyethoxy)ethyl]-S-methyl-sulfonimidoyl]phenyl]-N,N-dipropyl-3H-1-benzazepine-4-carboxamide

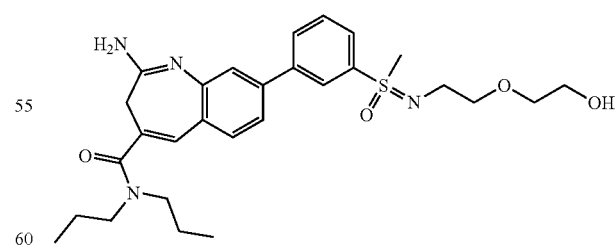

The title compound was prepared according to the general synthetic route shown in Scheme 1. A detailed synthetic route is provided in Scheme 5.

Scheme 5:

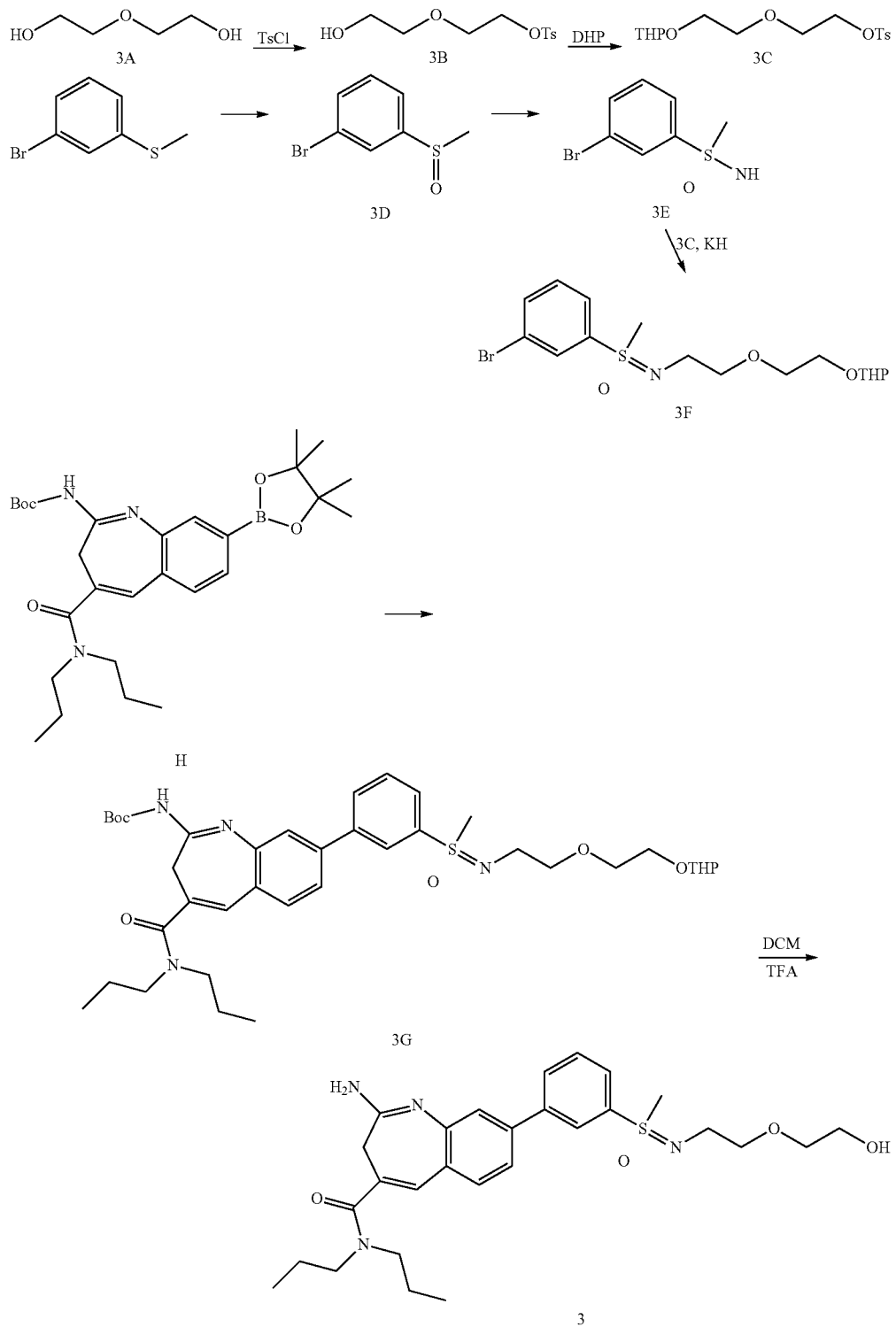

Step 1: Preparation of Compound 3B

To a stirred solution of diethylene glycol (compound 3A, 10.0 g, 94.2 mmol), Et$_3$N (2.86 g, 28.3 mmol) in DCM (50 mL) was added a solution of 4-methylbenzenesulfonyl chloride (4.49 g, 23.6 mmol) in DCM (50 mL) slowly at 16° C. Then the reaction mixture was stirred for 18 hours at 16° C. TLC (PE:EA=1:1) showed that the reaction was completed. The reaction mixture was washed with saturated NaHCO$_3$ (50 mL×2). The organic layer was dried over anhydrous Na$_2$SO$_4$ and concentrated in vacuo to give the crude product. The crude product was purified by silica gel chromatography (PE:EA=5:1-1:1) to give 2-(2-hydroxyethoxy)ethyl 4-methylbenzenesulfonate (compound 3B, 2.4 g, 39%) as colorless oil. MS: calc'd 278 (M+H$_2$O)$^+$, measured 278 (M+H$_2$O)$^+$.

Step 2: Preparation of Compound 3C

Over a period of 5 minutes, dihydropyran (2.5 g, 29.7 mmol) was added drop-wise to a stirred solution of 2-(2-hydroxyethoxy)ethyl 4-methylbenzenesulfonate (compound 3B, 2.40 g, 9.2 mmol) and p-toluenesulfonic acid monohydrate (125 mg, 0.66 mmol) in anhydrous dioxane (25 mL) at 20° C. After stirring for 20 minutes, saturated Na$_2$CO$_3$ was added until the solution was slightly basic. The mixture was concentrated under reduced pressure. The residue was dissolved in CH$_2$Cl$_2$ (50 mL), washed with brine (2×50 mL), dried over Na$_2$SO$_4$ and concentrated in vacuo. The residue was purified by silica gel column chromatography (PE:EA=20:1~10:1) to give 2-(2-((tetrahydro-2H-pyran-2-yl)oxy)ethoxy)ethyl 4-methylbenzenesulfonate (compound 3C, 2.3 g, 72.4%) as a colorless oil. MS: calc'd 262.1 (M+H$_2$O)$^+$, 267 (M+Na+); measured 262.2 (M+H$_2$O)$^+$, 267 (M+Na$^+$).

Step 3: Preparation of Compound 3D

To a solution of (3-bromophenyl)(methyl)sulfane (5.0 g, 24.7 mmol) in DCM (75 ml) was added m-CPBA (4.47 g, 25.9 mmol) at 0° C. After the reaction was stirred at 20° C. for 18 hours, it was quenched with aq. NaHSO$_3$ (30 mL) and aq.NaHCO$_3$ (30 mL). The organic layer was separated, washed with brine and dried over anhydrous Na$_2$SO$_4$. The organic layer was concentrated in vacuo and the residue was purified by trituration (PE:EA=10 mL, 1:9) to give 1-bromo-3-(methylsulfinyl)benzene (compound 3D, 3.8 g, 71.1%) as a white solid. MS: calc'd 219 (M+H)$^+$, measured 219 (M+H)$^+$.

Step 4: Preparation of Compound 3E

To a solution of 1-bromo-3-(methylsulfinyl)benzene (compound 3D, 3.8 g, 17.4 mmol) in Eaton's regent (30 mL) was added NaN$_3$ (3.4 mg, 52.3 mmol). After the reaction mixture was stirred at 60° C. for 20 min, it was poured into 1 M ammonium hydroxide solution at 0° C. The mixture was extracted with DCM (30 mL×2). The organic layer was washed with brine, dried over anhydrous Na$_2$SO$_4$ and concentrated to give 1-bromo-3-(S-methylsulfonimidoyl)benzene (compound 3E, 2.0 g, 48.7%) as a yellow solid. MS: calc'd 234 (M+H)+; measured 234 (M+H)$^+$.

Step 5: Preparation of Compound 3F

A solution of 1-bromo-3-(S-methylsulfonimidoyl)benzene (compound 3E, 500 mg, 2.14 mmol) in DME (15 mL) was added KH (269 mg, 2.35 mmol) at 0° C. After the mixture was stirred at 16° C. for 3 hours under nitrogen atmosphere, tetrabutylammonium bromide (28 mg, 0.10 mmol) and 2-(2-((tetrahydro-2H-pyran-2-yl)oxy)ethoxy)ethyl 4-methylbenzenesulfonate (compound 3C, 737 mg, 2.14 mmol) in DME (10 mL) was added into the reaction mixture. After the mixture was stirred at 30° C. for 16 hours, it was poured into water (30 mL). The mixture was extracted with EA (20 mL×3). The combined organic layers were washed with brine, dried over anhydrous Na$_2$SO$_4$ and concentrated to give the crude product. The crude product was purified by silica gel chromatography (PE:EA=4:1-2:1-1:1) to give (3-bromophenyl)-methyl-oxo-[2-(2-tetrahydropyran-2-yloxyethoxy)ethylimino]-sulfane (compound 3F, 240 mg, 27.6%) as a brown oil. MS: calc'd 406 (M+H)+; measured 406 (M+H)$^+$.

Step 6: Preparation of Compound 3G

A solution of tert-butyl N-[4-(dipropylcarbamoyl)-8-(4,4,5,5-tetramethyl-1,3,2-dioxaborolan-2-yl)-3H-1-benzazepin-2-yl]carbamate (compound H, 310 mg, 0.606 mmol), (3-bromophenyl)-methyl-oxo-[2-(2-tetrahydropyran-2-yloxyethoxy)ethylimino]-sulfane (compound 3F, 190 mg, 0.467 mmol), Na$_2$CO$_3$ (141 mg, 1.333 mmol) and Pd(dppf)Cl$_2$ (58 mg, 0.079 mmol) in dioxane/H$_2$O (7.5 mL/1.5 mL) was stirred at 50° C. for 16 hours under nitrogen atmosphere. The residue was diluted with EA (10 mL) and the precipitate was filtered. The solvent was removed in vacuo and the residue was purified by silica gel chromatography (PE:EA=1:1-100% EA) to give tert-butyl (4-(dipropylcarbamoyl)-8-(3-(S-methyl-N-(2-(2-((tetrahydro-2H-pyran-2-yl)oxy)ethoxy)ethyl)sulfonimidoyl)phenyl)-3H-benzo[b]azepin-2-yl)carbamate (compound 3G, 160 mg) as brown semi-solid. MS: calc'd 711 (M+H)+; measured 711 (M+H)+.

Step 7: Preparation of Example 3

A solution of TFA (513 mg, 4.5 mmol) in DCM (0.5 mL) was added drop-wise to a solution of tert-butyl (4-(dipropylcarbamoyl)-8-(3-(S-methyl-N-(2-(2-((tetrahydro-2H-pyran-2-yl)oxy)ethoxy)ethyl)sulfonimidoyl)phenyl)-3H-benzo[b]azepin-2-yl)carbamate (compound 3G, 160 mg, 0.225 mmol) in DCM (2 mL) at 0° C. Then the mixture was stirred for 3 hours at 20° C. The solution was neutralized with NaHCO$_3$ (about 450 mg) and the precipitate was filtered. The filtrate was concentrated and the residue was purified by pre-HPLC (base system) to give 2-amino-8-[3-[N-[2-(2-hydroxyethoxy)ethyl]-S-methyl-sulfonimidoyl]phenyl]-N,N-dipropyl-3H-1-benzazepine-4-carboxamide (Example 3, 10.3 mg) as a yellow solid. $^1$HNMR (400 MHz, METHANOL-d4) δ ppm=8.21 (s, 1H), 8.06-7.98 (m, 1H) 7.96-7.91 (m, 1H), 7.78-7.70 (m, 1H), 7.46 (d, J=12.30 Hz, 2H), 7.42-7.35 (m, 1H), 6.93-6.86 (m, 1H), 3.69-3.49 (m, 7H), 3.48-3.39 (m, 4H), 3.24 (s, 3H), 3.18-3.10 (m, 1H), 3.09-2.99 (m, 1H), 2.92-2.83 (m, 1H), 1.75-1.62 (m, 4H), 1.05-0.78 (m, 6H). MS: calc'd 527 (M+H)$^+$, measured 527 (M+H)$^+$.

Example 4

2-Amino-8-(5-methylsulfinyl-3-pyridyl)-N,N-dipropyl-3H-1-benzazepine-4-carboxamide

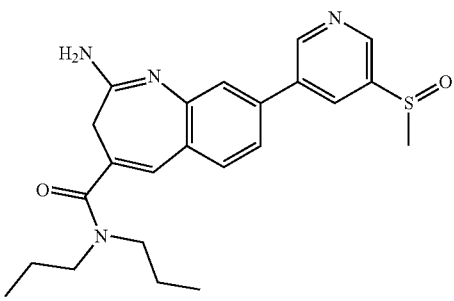 [SMILES: CCCN(CCC)C(=O)C1=Cc2ccc(-c3cncc(S(C)=O)c3)cc2N=C(N)C1]

The title compound was prepared in analogy to Example 1 by using 3-bromo-5-methylsulfanyl-pyridine instead of 1-bromo-4-methylsulfanyl-benzene. Example 4 was obtained as a yellow solid (4.7 mg). $^1$H NMR (400 MHz, METHANOL-d4) δ ppm=9.06 (d, J=2.0 Hz, 1H), 8.78-8.93 (m, 1H), 8.45 (t, J=2.1 Hz, 1H), 7.36-7.56 (m, 3H), 6.92 (s, 1H), 3.38-3.51 (m, 6H), 2.85-3.04 (m, 3H), 1.53-1.78 (m, 4H), 0.53-1.13 ppm (m, 6H). MS: calc'd 425 (M+H)$^+$, measured 425 (M+H)$^+$.

Example 5

2-Amino-8-(3-methylsulfinylphenyl)-N,N-dipropyl-3H-1-benzazepine-4-carboxamide

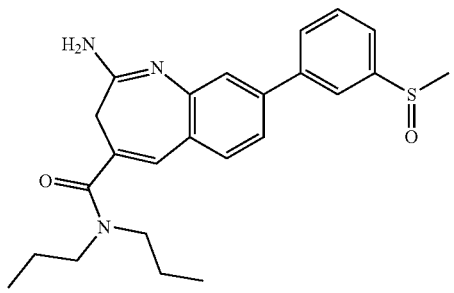 [SMILES: CCCN(CCC)C(=O)C1=Cc2ccc(-c3cccc(S(C)=O)c3)cc2N=C(N)C1]

The title compound was prepared in analogy to Example 1 by using 1-bromo-3-methylsulfanyl-benzene instead of 1-bromo-4-methylsulfanyl-benzene. Example 5 was obtained as a yellow solid (40 mg). $^1$H NMR (400 MHz, METHANOL-d4) δ ppm=8.02 (s, 1H), 7.85-7.93 (m, 1H), 7.64-7.76 (m, 2H), 7.32-7.49 (m, 3H), 6.90 (s, 1H), 3.45 (m, 6H), 2.74 (s, 3H), 1.54-1.75 (m, 4H), 0.57-1.14 ppm (m, 6H). MS: calc'd 424 (M+H)$^+$, measured 424 (M+H)$^+$.

Example 6

2-Amino-8-[5-(methylsulfonimidoyl)-3-pyridyl]-N,N-dipropyl-3H-1-benzazepine-4-carboxamide

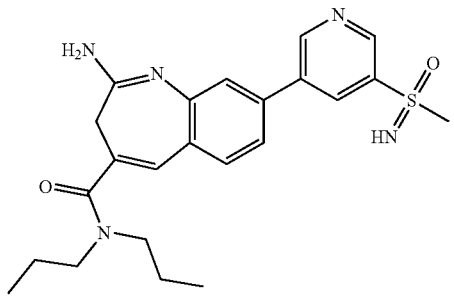 [SMILES: CCCN(CCC)C(=O)C1=Cc2ccc(-c3cncc(S(C)(=N)=O)c3)cc2N=C(N)C1]

The title compound was prepared in analogy to Example 2 by using 3-bromo-5-methylsulfanyl-pyridine instead of 1-bromo-4-methylsulfanyl-benzene. Example 6 was obtained as a yellow solid (8 mg). $^1$H NMR (400 MHz, METHANOL-d4) δ ppm=9.14-9.25 (m, 2H), 8.66 (t, J=2.1 Hz, 1H), 7.54-7.81 (m, 3H), 6.99-7.11 (m, 1H), 3.39-3.56 (m, 6H), 3.26 (s, 3H), 1.72 (m, 4H), 0.9δ ppm (m, 6H). MS: calc'd 440 (M+H)$^+$, measured 440 (M+H)$^+$.

Example 7

22-Amino-8-[3-(methylsulfonimidoyl)phenyl]-N,N-dipropyl-3H-1-benzazepine-4-carboxamide

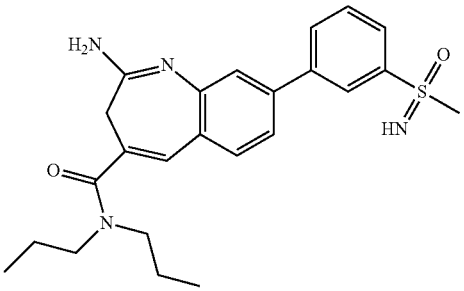 [SMILES: CCCN(CCC)C(=O)C1=Cc2ccc(-c3cccc(S(C)(=N)=O)c3)cc2N=C(N)C1]

The title compound was prepared in analogy to Example 2 by using 1-bromo-3-methylsulfanyl-benzene instead of 1-bromo-4-methylsulfanyl-benzene. Example 7 was obtained as a yellow solid (8.3 mg). $^1$H NMR (400 MHz, METHANOL-d4) δ ppm=8.34 (t, J=1.6 Hz, 2H), 8.01-8.15 (m, 2H), 7.59-7.84 (m, 3H), 7.10 (s, 1H), 3.41-3.59 (m, 6H), 3.25 (s, 3H), 1.72 (sxt, J=7.5 Hz, 4H), 0.97 ppm (br. s., 6H). MS: calc'd 439 (M+H)$^+$, measured 439 (M+H)$^+$.

Example 8

2-Amino-8-(4-ethylsulfinylphenyl)-N,N-dipropyl-3H-1-benzazepine-4-carboxamide

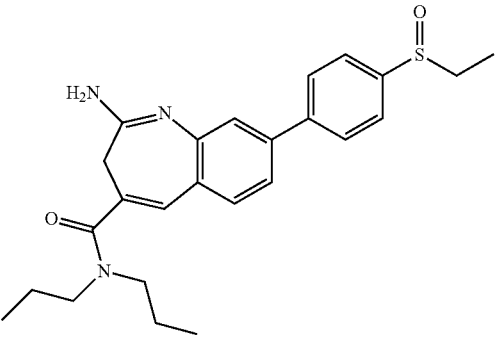 [SMILES: CCCN(CCC)C(=O)C1=Cc2ccc(-c3ccc(S(=O)CC)cc3)cc2N=C(N)C1]

The title compound was prepared in analogy to Example 1 by using 1-bromo-4-ethylsulfanyl-benzene instead of 1-bromo-4-methylsulfanyl-benzene. Example 8 was obtained as a yellow solid (45 mg). $^1$H NMR (400 MHz, METHANOL-d4) δ ppm=7.91-8.01 (m, 2H), 7.56-7.86 (m, 5H), 7.03-7.15 (m, 1H), 3.49 (br. s., 4H), 3.35-3.40 (m, 2H), 2.80-2.98 (m, 2H), 1.62-1.82 (m, 4H), 1.14-1.30 (m, 3H), 0.97 ppm (br. s, 6H). MS: calc'd 438 (M+H)$^+$, measured 438 (M+H)$^+$.

Example 9

2-Amino-8-[4-(ethylsulfonimidoyl)phenyl]-N,N-dipropyl-3H-1-benzazepine-4-carboxamide

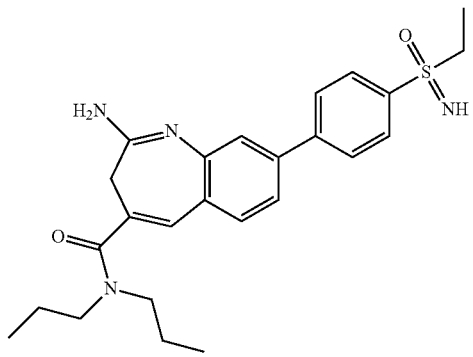 [SMILES: CCCN(CCC)C(=O)C1=Cc2ccc(-c3ccc(S(=N)(=O)CC)cc3)cc2N=C(N)C1]

The title compound was prepared in analogy to Example 2 by using 1-bromo-4-ethylsulfanyl-benzene instead of 1-bromo-4-methylsulfanyl-benzene. Example 9 was obtained as a yellow solid (5 mg). $^1$H NMR (400 MHz, METHANOL-d4) δ ppm=8.09 (d, J=8.3 Hz, 2H), 7.87-8.02 (m, 2H), 7.55-7.77 (m, 3H), 7.07 (s, 1H), 3.40-3.60 (m, 4H), 3.22-3.31 (m, 2H), 2.66-2.77 (m, 2H), 1.72 (sxt, J=7.5 Hz, 4H), 1.13-1.33 (m, 3H), 0.97 ppm (br. s., 6H). MS: calc'd 453 (M+H)$^+$, measured 453 (M+H)$^+$.

Example 10

2-Amino-8-(3-ethylsulfinylphenyl)-N,N-dipropyl-3H-1-benzazepine-4-carboxamide

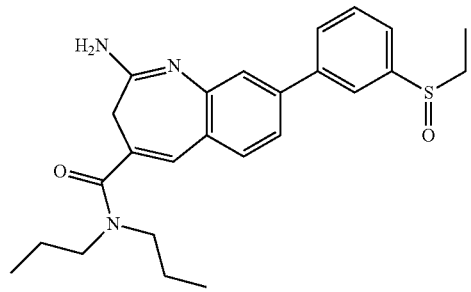 [SMILES: CCCN(CCC)C(=O)C1=Cc2ccc(-c3cccc(S(=O)CC)c3)cc2N=C(N)C1]

The title compound was prepared in analogy to Example 1 by using 1-bromo-3-ethylsulfanyl-benzene instead of 1-bromo-4-methylsulfanyl-benzene. Example 10 was obtained as a yellow solid (29 mg). $^1$H NMR (400 MHz, METHANOL-d4) δ ppm=7.85-8.08 (m, 2H), 7.53-7.79 (m, 5H), 6.94-7.13 (m, 1H), 3.49 (br. s., 4H), 3.05-3.20 (m, 2H), 2.77-3.04 (m, 2H), 1.54-1.83 (m, 4H), 1.14-1.32 (m, 3H), 0.97 ppm (br. s., 6H). MS: calc'd 438 (M+H)$^+$, measured 438 (M+H)$^+$.

Example 11

2-Amino-8-[3-(ethylsulfonimidoyl)phenyl]-N,N-dipropyl-3H-1-benzazepine-4-carboxamide

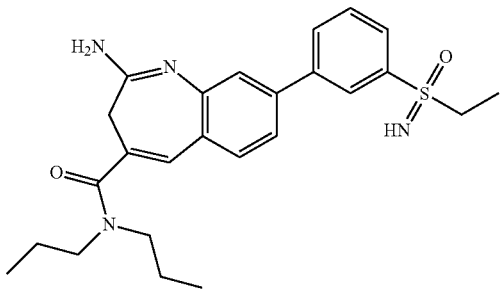 [SMILES: CCCN(CCC)C(=O)C1=Cc2ccc(-c3cccc(S(=N)(=O)CC)c3)cc2N=C(N)C1]

The title compound was prepared in analogy to Example 2 by using 1-bromo-3-ethylsulfanyl-benzene instead of 1-bromo-4-methylsulfanyl-benzene. Example 11 was obtained as a yellow solid (5 mg). $^1$H NMR (400 MHz, METHANOL-d4) δ ppm=8.30 (t, J=1.6 Hz, 1H), 8.09 (dd, J=15.6, 8.3 Hz, 2H), 7.59-7.85 (m, 4H), 7.12 (s, 1H), 3.50 (br. s., 4H), 3.36-3.44 (m, 4H), 2.64-2.77 (m, 2H), 1.73 (sxt, J=7.4 Hz, 3H), 1.18-1.32 (m, 2H), 0.97 ppm (br. s., 6H). MS: calc'd 453 (M+H)$^+$, measured 453 (M+H)$^+$.

We claim:
1. A compound of the formula

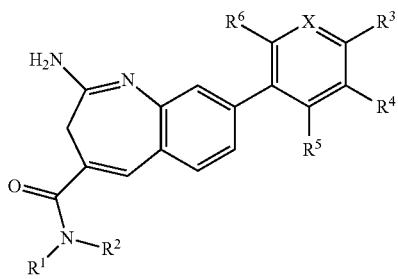

wherein
X is C—R$^7$ or N;
R$^1$ is C$_{3-7}$-alkyl or C$_{3-7}$-cycloalkyl,
R$^2$ is selected from the group consisting of C$_{3-7}$-alkyl, hydroxy-C$_{1-7}$-alkyl, C$_{3-7}$-alkynyl, amino-C$_{1-7}$-alkoxy-C$_{1-7}$-alkoxy-C$_{1-7}$-alkyl, halogen-C$_{1-7}$-alkyl and C$_{3-7}$-cycloalkyl-C$_{1-7}$-alkyl;
one of R$^3$ and R$^4$ is

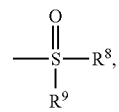

and the other one of R$^3$ and R$^4$ is selected from the group consisting of hydrogen, C$_{1-7}$-alkyl and halogen;
R$^5$, R$^6$ and R$^7$ are independently from each other selected from hydrogen, C$_{1-7}$-alkyl and halogen;
R$^8$ is C$_{1-7}$-alkyl;

$R^9$ is absent or is =N—$R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl, or pharmaceutically acceptable salts thereof.

2. The compound of formula I according to claim 1, wherein $R^1$ is propyl.

3. The compound of formula I according to claim 1 wherein $R^2$ is propyl.

4. The compound of formula I according to claim 1 wherein $R^3$ is selected from the group consisting of hydrogen, $C_{1-7}$-alkyl and halogen and
$R^4$ is

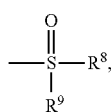

wherein $R^8$ is $C_{1-7}$-alkyl and $R^9$ is absent or is =N—$R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl.

5. The compound of claim 4, wherein $R^3$ is hydrogen.

6. The compound of formula I according to claim 1, wherein $R^4$ is selected from the group consisting of hydrogen, $C_{1-7}$-alkyl and halogen and
$R^3$ is

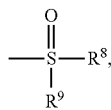

wherein $R^8$ is $C_{1-7}$-alkyl and $R^9$ is absent or is =N—$R^{10}$, wherein $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl.

7. The compound of claim 6, wherein $R^4$ is hydrogen.

8. The compound according to claim 1, wherein $R^5$ and $R^6$ are hydrogen.

9. The compound of formula I according to claim 1, wherein one of $R^3$ or $R^4$ is

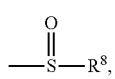

wherein $R^8$ is $C_{1-7}$-alkyl.

10. The compound of formula I according claim 1, wherein
one of $R^3$ and $R^4$ is

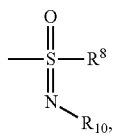

wherein $R^8$ is $C_{1-7}$-alkyl; and $R^{10}$ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl.

11. The compound of formula I according to claim 1, wherein $R^{10}$ is hydrogen or hydroxy-$C_{1-7}$-alkoxy-$C_{1-7}$-alkyl.

12. The compound of formula I according to claim 1, wherein $R^8$ is methyl or ethyl.

13. The compound of formula I according to claim 1, wherein X is C—$R^7$ and $R^7$ is hydrogen.

14. The compound of formula I according to claim 1, wherein X is N.

15. The compound of formula I according to claim 1, selected from the group consisting of:
2-amino-8-(4-methylsulfinylphenyl)-N,N-dipropyl-3H-1-benzazepine-4-carboxamide,
2-amino-8-[4-(methylsulfonimidoyl)phenyl]-N,N-dipropyl-3H-1-benzazepine-4-carboxamide,
2-amino-8-[3-[N-[2-(2-hydroxyethoxy)ethyl]-S-methyl-sulfonimidoyl]phenyl]-N,N-dipropyl-3H-1-benzazepine-4-carboxamide,
2-amino-8-(5-methylsulfinyl-3-pyridyl)-N,N-dipropyl-3H-1-benzazepine-4-carboxamide,
2-amino-8-(3-methylsulfinylphenyl)-N,N-dipropyl-3H-1-benzazepine-4-carboxamide,
2-amino-8-[5-(methylsulfonimidoyl)-3-pyridyl]-N,N-dipropyl-3H-1-benzazepine-4-carboxamide,
2-amino-8-[3-(methylsulfonimidoyl)phenyl]-N,N-dipropyl-3H-1-benzazepine-4-carboxamide,
2-amino-8-(4-ethylsulfinylphenyl)-N,N-dipropyl-3H-1-benzazepine-4-carboxamide,
2-amino-8-[4-(ethylsulfonimidoyl)phenyl]-N,N-dipropyl-3H-1-benzazepine-4-carboxamide,
2-amino-8-(3-ethylsulfinylphenyl)-N,N-dipropyl-3H-1-benzazepine-4-carboxamide, and,
2-amino-8-[3-(ethylsulfonimidoyl)phenyl]-N,N-dipropyl-3H-1-benzazepine-4-carboxamide, or pharmaceutically acceptable salts thereof.

16. The compound of formula I according to claim 1, selected from the group consisting of
2-amino-8-(5-methylsulfinyl-3-pyridyl)-N,N-dipropyl-3H-1-benzazepine-4-carboxamide,
2-amino-8-(3-methylsulfinylphenyl)-N,N-dipropyl-3H-1-benzazepine-4-carboxamide, and
2-amino-8-(3-ethylsulfinylphenyl)-N,N-dipropyl-3H-1-benzazepine-4-carboxamide, or pharmaceutically acceptable salts thereof.

17. A pharmaceutical composition comprising a compound of formula I according to claim 1 and at least one pharmaceutically acceptable carrier and/or adjuvant.

18. A method for treatment sepsis mediated by a TLR agonist comprising administering to a patient in need thereof a therapeutically effective amount of a compound according to claim 1.

19. A process for the manufacture of a compound of formula I as defined in claim 1, which process comprises reacting a compound of the formula II

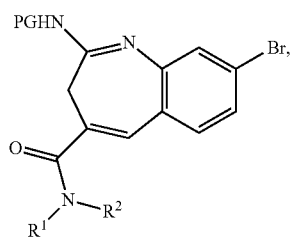

wherein,

R¹ is $C_{3-7}$-alkyl or $C_{3-7}$-cycloalkyl,

R² is selected from the group consisting of $C_{3-7}$-alkyl, hydroxy-$C_{1-7}$-alkyl, $C_{3-7}$-alkynyl, amino-$C_{1-7}$-alkoxy-$C_{1-7}$-alkoxy-$C_{1-7}$-alkyl, halogen-$C_{1-7}$-alkyl and $C_{3-7}$-cycloalkyl-$C_{1-7}$-alkyl; and PG is a protecting group, with bis(pinacolato)diboron under basic conditions in the presence of a Pd catalyst to obtain a boronic ester of the formula III

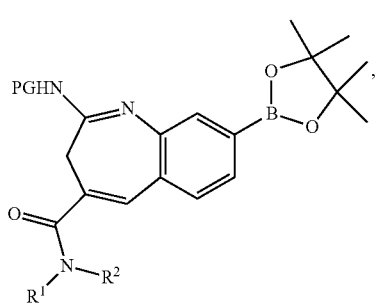

III and coupling the compound III under basic conditions in the presence of a Pd catalyst with a bromide of the formula IV

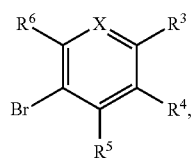

IV wherein:

X is C—R⁷ or N;

one of R³ and R⁴ is

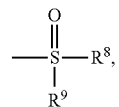

and the other one of R³ and R⁴ is selected from the group consisting of hydrogen, $C_{1-7}$-alkyl and halogen;

R⁵, R⁶ and R⁷ are independently from each other selected from hydrogen, $C_{1-7}$-alkyl and halogen;

R⁸ is $C_{1-7}$-alkyl;

R⁹ is absent or is =N—R¹⁰, wherein R¹⁰ is selected from the group consisting of hydrogen, $C_{1-7}$-alkyl, halogen-$C_{1-7}$-alkyl, hydroxy-$C_{1-7}$-alkyl and hydroxy-$C_{1-7}$-alkoxy-$C_{1-7}$-alkyl, and subsequently removing the protecting group PG under acidic conditions to obtain a compound of the formula I

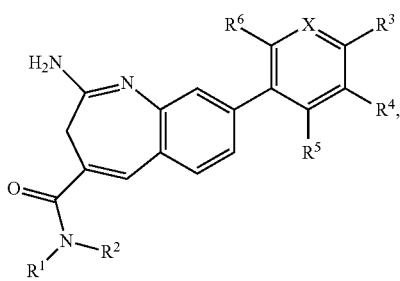

I and, if desired, converting the compound obtained into a pharmaceutically acceptable salt.

* * * * *